United States Patent [19]

Werner

[11] Patent Number: 4,625,035

[45] Date of Patent: Nov. 25, 1986

[54] 2,3-DIFLUORO-5-(TRIFLUOROMETHYL)-PYRIDINE

[75] Inventor: John A. Werner, Palo Alto, Calif.

[73] Assignee: The Dow Chemical Company, Midland, Mich.

[21] Appl. No.: 789,791

[22] Filed: Oct. 21, 1985

Related U.S. Application Data

[60] Continuation-in-part of Ser. No. 621,343, Jun. 18, 1984, abandoned, which is a division of Ser. No. 401,057, Jul. 23, 1982, Pat. No. 4,480,102.

[51] Int. Cl.$^4$ .............................................. C07D 213/26
[52] U.S. Cl. ..................................... 546/345; 546/346
[58] Field of Search ................................ 546/346, 345

[56] References Cited

U.S. PATENT DOCUMENTS 4,184,041  1/1980  Nishiyama et al. ................. 546/345
4,279,913  7/1981  Baldwin et al. ..................... 514/309

FOREIGN PATENT DOCUMENTS 2015995A  9/1979  United Kingdom ................ 546/302

Primary Examiner—Alan L. Rotman
Attorney, Agent, or Firm—Merlin B. Davey

[57] ABSTRACT

Novel 2,3-difluoro-5-(trifluoromethyl)pyridine is prepared by fluorinating 3-chloro-2-fluoro-5-(trifluoromethyl)pyridine under favorable conditions. The compound is useful as a chemical intermediate in the preparation of herbicides.

1 Claim, No Drawings

2,3-DIFLUORO-5-(TRIFLUOROMETHYL)PYRIDINE

CROSS-REFERENCE TO RELATED APPLICATIONS

This application is a continuation-in-part of application Ser. No. 621,343 filed June 18, 1984, now abandoned, which in turn is a division of application Ser. No. 401,057 filed July 23, 1982, now U.S. Pat. No. 4,480,102.

BACKGROUND OF THE INVENTION

The present invention is directed to 2,3-difluoro-5-(trifluoromethyl)pyridine.

Pyridyloxyphenoxy alkanoic acids and their derivatives are known herbicidal agents. 2-(4-((3-Chloro-5-(trifluoromethyl)-2-pyridinyl)oxy)phenoxy)propanoic acid and derivatives and 2-(4-((5-(trifluoromethyl)-2-pyridinyl)oxy)phenoxy)propanoic acid and derivatives are promising herbicides in the developmental stages of commercialization. In copending application Ser. No. 389,840 filed 18 June 1982, now abandoned in favor of continuation-in-part application Ser. No. 497,295 filed May 23, 1983, it is shown that pyridyloxy phenoxy alkanoic acids having a fluoro in the 3-position of the pyridine ring have unexpectedly superior herbicidal activity. It has further been found that such compounds have reduced toxicity to warm-blooded animals as compared, e.g. to similar compounds having chlorine in the 3-position of the pyridine ring. The present compound, i.e., 2,3-difluoro-5-(trifluoromethyl)pyridine, is a valuable chemical intermediate which can be used in preparing 2-(4-((3-fluoro-5-(trifluoromethyl)-2-pyridinyl)oxy)-phenoxy)alkanoic acids and derivatives thereof. Additionally, the compound of the present invention provides an intermediate which reacts more readily with 2-(4-hydroxyphenoxy)propionic acid and derivatives thereof, resulting in a higher yield of end product when compared to intermediates containing chloro or bromo in the 2 position of the pyridine ring.

SUMMARY OF THE INVENTION

The present invention is directed to 2,3-difluoro-5-(trifluoromethyl)pyridine which may be used as a chemical intermediate in preparing 2-(4-((3-fluoro-5-(trifluoromethyl)-2-pyridinyl)oxy or thio)phenoxy)alkanoic acid herbicides and derivatives thereof.

The present invention also provides a method of preparing 2,3-difluoro-5-(trifluoromethyl)pyridine by employing an halogen exchange reaction via a nucleophilic aromatic substitution at the 3-position of the pyridine ring. The presently claimed compound may be prepared by reacting 3-chloro-2-fluoro-5-(trifluoromethyl)pyridine with CsF in a solvent under conditions favorable to form the desired product.

2,3-Difluoro-5-(trifluoromethyl)pyridine is a colorless liquid having a boiling point of 104° C. @760 mm Hg and a refractive index of (n19/D) 1.3885.

DETAILED DESCRIPTION OF THE INVENTION 2,3-Difluoro-5-(trifluoromethyl)pyridine may be prepared by reacting 2-fluoro-3-chloro-5-(trifluoromethyl)pyridine with at least about an equimolar amount of CsF. Preferably the reaction is carried out in a solvent or reaction medium such as, dimethylsulfoxide (DMSO), N-methylpyrrolidinone, dimethylformamide (DMF), hexamethylphosphoramide (HMPA) or sulfolane. The temperature at which the reaction is conducted is not critical but usually is between about 85° C. and about 180° C. and preferably between about 120° and about 170° C. Depending upon which solvent is employed in a particular reaction, the optimum temperature will vary. For example, when employing DMSO, a preferred temperature to conduct the reaction will be from about 120° C. to about 140° C., and, when employing sulfolane, a preferred temperature to conduct the reaction will be from about 150° C. to about 170° C. Generally speaking the lower the temperature the slower reaction will proceed. The present reaction is typically conducted in the presence of vigorous agitation sufficient to maintain an essentially uniformly dispersed mixture of the reactants.

In conducting the present reaction neither the rate of addition of the reactants nor the order of addition of the reactants is critical. Usually, the solvent and CsF are mixed before the 3-chloro-2-fluoro-5-(trifluoromethyl)-pyridine is added to the reaction mixture. A typical reaction generally requires from about 4 to about 100 hours and is usually conducted at ambient atmospheric pressure.

While the exact amount of reactants is not critical, it is preferred to employ an amount of CsF which will supply at least about an equimolar amount of fluorine atoms based on the molar amount of 3-chloro-2-fluoro-5-(trifluoromethyl)pyridine starting material, i.e., at least about an equimolar amount of CsF. After the reaction is completed the desired product is recovered by employing standard separation and purification techniques, such as, distillation.

Alternatively, the 3-chloro-2-fluoro-5-(trifluoromethyl)pyridine starting material may be formed in situ by fluorinating known compounds, such as, 2,3-dichloro-5-(trifluoromethyl)pyridine or 2,3-dichloro-5-(trichloromethyl)pyridine employing well known procedures. (See, for example U.S. Pat. No. 4,184,041 and European Patent Application No. 80201077.7, Publication No. 0 028 870, published 20 May 1981). This reaction can be characterized as follows:

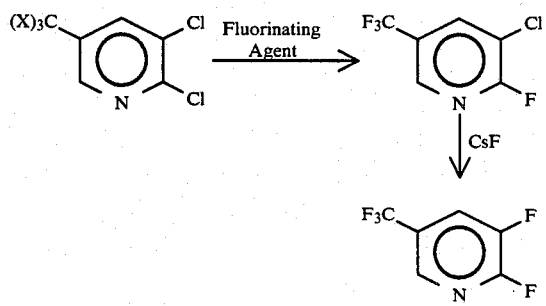

wherein each X is independently chloro or fluoro. The thus formed 3-chloro-2-fluoro-5-(trifluoromethyl)pyridine is then reacted with CsF under favorable conditions to form the desired product.

In a preferred embodiment of the present invention, 3-chloro-2-fluoro-5-(trifluoromethyl)pyridine is reacted with about a 50% molar excess of CsF in DMSO at a temperature between about 120° and 125° C. under constant agitation and at ambient atmospheric pressure. After about 48 hours, the reaction is stopped and the desired product recovered.

The following examples are merely representative of the present invention and, as such, should not be deemed as a limitation thereof. No attempt has been made to balance any chemical equations described herein.

EXAMPLE 1

Preparation of 2,3-difluoro-5-(trifluoromethyl)pyridine

A 100 milliliter (ml) 4-neck round bottom flask, equipped with an air-driven mechanical stirrer and fitted with a dry ice condenser, thermometer and sample port, was charged with 50 ml of dimethylsulfoxide (DMSO), 1.9 grams (g) (0.0125 mole) CsF and a pinch (~0.5 g) of $K_2CO_3$ (added to neutralize any acid present in the sample of 3-chloro-2-fluoro-5-(trifluoromethyl)pyridine) and heated to 115° C. under vacuum so that about 20 ml of DMSO was distilled off to dry the reaction mixture. The solution was light tan in appearance. Nitrogen was bled into the system and the temperature was reduced to about 70° C. To the reaction mixture was added 1.98 g (0.01 mole) of 3-chloro-2-fluoro-5-(trifluoromethyl)pyridine in one portion. The reaction mixture was heated to about 105° C. and constantly agitated for a total of 21 hours resulting in a black liquid. The formation of the desired product, i.e. 2,3-difluoro-5-(trifluoromethyl)pyridine, was confirmed by employing standard gas chromatography-mass spectrometry (g.c.-m.s.) procedures.

EXAMPLE 2

Preparation of 2,3-difluoro-5-(trifluoromethyl)pyridine

A 100 ml 4-neck round bottom flask, containing a magnetic stir bar and fitted with a thermometer, nitrogen inlet and distillation condenser, was charged with 75 ml of DMSO, 0.5 g of anhydrous $K_2CO_3$ and 22.8 g (0.15 mole) of CsF. The reaction mixture was heated to 115° C. at 57 mm Hg so that about 20 ml of DMSO was distilled to dry the reaction mixture. The light yellow reaction mixture was cooled to 65° C. and 20 g (0.1 mole) of 3-chloro-2-fluoro-5-(trifluoromethyl)pyridine was added through a pressure equalizing addition funnel which replaced the distillation condenser. After a dry ice condenser was attached to the flask the reaction temperature was maintained at 105°-115° C. for 46.5 hours with constant agitation. The reaction mixture was black with dark solids on the sides of the flask. A short path distillation condenser was attached to the flask and 13 g of crude product was collected in a receiver, which was cooled in a dry ice/acetone bath (pressure=210 mm Hg; temperature (overhead)=85°-130° C.; temperature (pot)=125°-160° C.). This crude product was extracted with water to remove any residual DMSO and dried over 4 Å molecular sieves (11.5 g crude product; 11 g crude product after drying). The product was then transferred to a 25 ml round bottom flask and distilled at 102° C. (uncorrected)/760 mm Hg through a Vigreaux ® column resulting in 9.3 g of substantially pure 2,3-di-fluoro-5-(trifluoromethyl)pyridine. The isolated yield of desired product was calculated to be 48.4% of theoretical. The structure of the product was confirmed by its nuclear magnetic resonance (NMR) spectra. Elemental analysis results for the product were: Theoretical: C, 39.36; H, 1.09; N, 7.65; Cl, 0. Found: C, 38.44; H, 1.01; N, 7.79; Cl, 0.25.

EXAMPLE 3

Preparation of 2,3-difluoro-5-(trifluoromethyl)pyridine

A 500 ml 4-neck round bottom flask, equipped with an air driven mechanical stirrer and fitted with a thermometer, a distillation condenser and a stopper, was charged with 500 ml of DMSO, 1 g anhydrous $K_2CO_3$ and 25 g (0.165 mole) of CsF (one third of total CsF). The flask was heated with a heating mantle and about 100 ml of DMSO was distilled at ~110° C./~40 mm Hg to dry the reaction mixture. The reaction mixture was cooled to about 75° C. and $N_2$ was reintroduced into the flask. The distillation condenser was replaced by a reflux condenser which was vented to a dry ice trap with a $N_2$ atmosphere. To the reaction mixture was added 65.7 g of 3-chloro-2-fluoro-5-(trifluoromethyl)pyridine (0.329 mole) in one portion, with constant agitation, and the temperature of the reaction mixture was increased to between 120°-125° C. with the aid of a Thermowatch ® temperature controller. In 2.5 hours and 21.5 hours after the addition of the 3-chloro-2-fluoro-5-(trifluoromethyl)pyridine, additional 25 g portions of CsF were added to the reaction mixture for a total of 75 g of CsF in the reaction mixture. The reaction was allowed to run 69 hours at which time the reaction mixture appeared black with dark solids on the walls of the flask. A distillation condenser was attached to the flask and the reflux condenser was removed to allow the removal of the crude product by distillation (pressure=210 mm Hg; temperature (overhead)=90°-130° C.; temperature (pot)=~160° C.). To prevent the volatile product from being lost, the receiver was cooled in a dry ice/acetone bath. The distillation was continued until the head temperature stopped increasing at which time the vacuum was released, the receivers changed and the distillation resumed. An additional 10 ml was distilled over at a temperature of 130° C. and the distillation was stopped. The crude material was extracted with 100 ml of water and dried over 0.5 g of 4 Å molecular sieves to give 35.1 g of 2,3-difluoro-5-(trifluoromethyl)pyridine. Elemental analysis results of the product were: Found: C, 39.06; H, 1.15; N, 7.88; Cl, 0.15. Theoretical: C, 39.36; H, 1.09; N, 7.65; Cl, 0.

The present compound is useful as a chemical intermediate in the preparation of 2-(4-((3-fluoro-5-(trifluoromethyl)-2-pyridinyl)oxy)phenoxy)alkanoic acid herbicides and derivatives thereof. Such derivatives include salts, esters, ethers and amides of such alkanoic acid herbicides.

In one embodiment 2,3-difluoro-5-(trifluoromethyl)pyridine is reacted with the disodium salt of 2-(4-(hydroxyphenoxy)propanoic acid in a solvent, such as, dimethylsulfoxide, at an elevated temperature resulting in the formation of 2-(4-((3-fluoro-5-(trifluoromethyl)-2-pyridinyl)oxy)phenoxy)propanoic acid. This acid is then recovered employing well known techniques, or may be further modified, employing well known techniques, to form salts, esters, amides and ethers of the acid. It has been unexpectedly found that employing the present compound, i.e., 2,3-difluoro-5-(trifluoromethyl)pyridine, as the starting material results in a higher yield of the desired 2-(4-((3-fluoro-5-(trifluoromethyl)-2-pyridinyl)oxy)phenoxy)alkanoic acid or derivatives thereof as compared to when a 2-chloro- or 2-bromo-3-fluoro-5-(trifluoromethyl)pyridine compound is employed as a starting material.

EXAMPLE 4

Preparation of Propanoic Acid: 2-(4-((3-fluoro-5-(trifluoromethyl)-2-pyridinyl)oxy)-phenoxy) from 2,3-Difluoro-5-(trifluoromethyl)pyridine 2-(4-Hydroxyphenoxy)propanoic acid (6.0 g, 0.033 mole) was dissolved in 60 ml of dimethyl sulfoxide. The system was flushed with nitrogen and a solution of sodium hydroxide (2.64 g, 0.066 mole), dissolved in 3 ml of water, was added. The mixture was stirred and warmed for 26 minutes to a temperature of 57° C. A solution of 2,3-difluoro-5-(trifluoromethyl)pyridine (6.0 g, 0.0327 mole) in 7 ml of dimethyl sulfoxide was added over a 2 minute period. The temperature rose to 70° C. during the addition. The temperature was allowed to rise to 80° C. over the next 40 minutes at which time the reaction appeared to be complete.

The reaction mixture was poured into 250 ml of water and slowly acidified by adding a solution of hydrochloric acid (5 g of concentrated acid in 20 ml of water) dropwise, with good stirring. When the solution turned slightly cloudy, seed crystals were added; the acidification was completed to a pH of ~2. The free acid came down as a solid which was filtered off, rinsed with water and dried to yield 10.35 g of acid which had an elemental analysis of:

Found: C, 51.93; H, 3.15; N, 4.01. Theoretical: C, 52.18; H, 3.21; N, 4.06.

This material had a melting point of 132.5° C. to 133.5° C.

In similar operations, the present compound is employed in preparing 2-(4-((3-fluoro-5-(trifluoromethyl)-2-pyridinyl)thio)phenoxy)alkanoic acids and derivatives thereof which are also known herbicides.

I claim:

1. 2,3-Difluoro-5-(trifluoromethyl)pyridine.

* * * * *